(12) United States Patent
Legoupil

(10) Patent No.: US 7,623,226 B2
(45) Date of Patent: Nov. 24, 2009

(54) OPTICAL METHOD AND DEVICE FOR DETECTING SURFACE AND STRUCTURAL DEFECTS OF A TRAVELLING HOT PRODUCT

(75) Inventor: Jean-Luc Legoupil, Paris (FR)

(73) Assignee: Siemens VAI Metals Technologies SAS, Saint-Chamond (FR)

( * ) Notice: Subject to any disclaimer, the term of this patent is extended or adjusted under 35 U.S.C. 154(b) by 199 days.

(21) Appl. No.: 11/603,138

(22) Filed: Nov. 22, 2006

(65) Prior Publication Data

US 2007/0115473 A1     May 24, 2007

(30) Foreign Application Priority Data

Nov. 23, 2005   (FR)   ................................. 05 11997

(51) Int. Cl.
    *G01N 21/00*   (2006.01)
(52) U.S. Cl. .................. 356/237.1; 356/237.2
(58) Field of Classification Search ... 356/237.1–237.6, 356/51, 72; 382/312–318, 260; 359/201–202, 359/355; 250/208.1, 330, 342, 358.1, 359.1, 250/341.7
    See application file for complete search history.

(56) References Cited

U.S. PATENT DOCUMENTS

| 4,215,273 A | 7/1980 | Stokes et al. |
| 4,759,072 A | 7/1988 | Yamane et al. |
| 4,939,369 A * | 7/1990 | Elabd .......................... 250/332 |
| 5,373,182 A | 12/1994 | Norton |
| 5,654,977 A | 8/1997 | Morris |
| 5,690,430 A | 11/1997 | Rudolph |
| 6,486,974 B1 | 11/2002 | Nakai et al. |
| 6,784,996 B2 * | 8/2004 | Ikeda et al. ................. 356/406 |
| 2004/0125228 A1 | 7/2004 | Dougherty |

FOREIGN PATENT DOCUMENTS

| FR | 2768510 A1 | 3/1999 |
| WO | WO 02/25345 A3 | 3/2002 |

* cited by examiner

*Primary Examiner*—Michael A Lyons
*Assistant Examiner*—Tri T Ton
(74) *Attorney, Agent, or Firm*—Laurence A. Greenberg; Werner H. Stemer; Ralph E. Locher

(57) ABSTRACT

An optical method and device for detecting surface and structural defects of a traveling hot product, such as flat metal products during hot rolling, is disclosed. The optical method includes using images of the product from a camera and formed for one part by light for which the wavelength is in the infrared region and for another part by light for which the wavelength is in the visible spectrum. Detection of the images is provided by several linear sensors, each of them being associated with the detection of one image, each located in a different focal plane associated with each wavelength range so as to obtain superposable images. The light forming a portion of the images is sent onto the surface of the traveling product.

17 Claims, 3 Drawing Sheets

OPTICAL METHOD AND DEVICE FOR DETECTING SURFACE AND STRUCTURAL DEFECTS OF A TRAVELLING HOT PRODUCT

BACKGROUND (1) Field of the Invention

The present invention relates to an optical method and device for detecting surface and structural defects of a travelling hot product, it is particularly applied to metal products during hot-rolling and to flat metal products at the exit of a hot-rolling mill.

(2) Prior Art

The metal products are generally obtained from slabs and billets processed in continuous casting and then hot-rolled in a succession of rolling stands. Rolling is performed at high temperature, generally towards 1,000° C. when dealing with steel. But the invention may also apply to non-ferrous metals such as copper or aluminium, as well as to plastics.

By practicing the rolling of steel, the section of the product may be reduced while lengthening it along the longitudinal axis which is the axis of travel during rolling. With this method, particular mechanical properties with a certain axial isotropy may be given to the product.

But the method is not without drawbacks for the structure of the product, particularly of metal products and especially steel. Indeed, defects of different origins may be found associated in the structure of the product, it is possible to have surface defects caused by scale which remains adhered to the surface of the product and which originates from the oxidization of the surface caused by the water cooling of the rolling stands. Encrusted scale may also be found inside the product. Other defects may stem from difficulties encountered further upstream, such as bad lubrication upon casting the slab or heat shock during the cooling. These hazards of the manufacturing method may generate structural defects in the metal, which may be localized inside the thickness of the product as well at its surface.

Being able to detect surface defects and defects present under the surface is therefore important for all the products. When optical devices for detecting defects are set up in the hot-rolling facility, the latter may be detected by observing the light emitted by the product itself or that stemming from an auxiliary illumination source and reflected by the product. For example, specially developed optical devices are already known for detecting surface defects of flat products, using means for illuminating the surface and means for observing the reflected light. Observation of the emitted light in the visible light region gives good results for detecting surface defects but does not allow detection of defects localized under the surface. The idea was then devised of associating the observation of the light emitted by the product, which emits radiation in the infrared region because of its temperature, and of that which is emitted by an additional illumination, generally in the visible region and reflected by the surface of the product. The surface defects are the only ones which are detected by reflection of additional illumination, and defects present under the surface may be detected by proceeding with subtraction, as they are transmitted by the infrared light emitted by the core of the product.

A well-known optical problem is then posed, which is that of chromatic aberration of the lenses. Indeed, the images taken with the different lights must be able to be processed and compared, the defects under the surface being derived from the processing of the difference between both images. For this, sharp and superposable images must be obtained.

The problem of chromatic aberration is solved in different ways in conventional devices for shooting images. In a device of this type, the phenomenon leads to having sharp images in different focal planes according to the wavelength. In cameras for example, the combination of convergent lenses and divergent lenses, for which the phenomenon is inverted, may allow an image focal plane to be built in which both effects are cancelled out. One then has a lens called an achromatic lens. The diaphragm may also be used in order to increase the depth of field. Indeed, the objective of an image shooting device is calculated for its full aperture, i.e., for processing the light rays arriving over its entire surface. If the diaphragm is closed, the diameter of the aperture letting through the light rays is limited and the objective only operates in its central area for which these phenomena are reduced and the field of sharpness increases.

This property is further called depth of field, this means that the range of distances for which the image will be sharp in the image focal plane, is extended. But, for this, sufficient light should be available and this kind of devices was proposed by the applicant company for detecting defects of long iron and steel products which are narrow and therefore generate a concentrated image containing sufficient light. This is different for flat products for which the width of the dimension to be observed is larger and the light is less concentrated.

It would also be possible to vary the other image shooting parameter: the exposure time. Indeed, these automatic inspection devices use cameras fitted with photosensitive sensors which operate with a certain integration time. With this trick, a sufficient signal is obtained in the case of faint light. But the integration time is limited by the travelling speed of the product at which the observation must be made while retaining a sharp image. Now, it is found that today, flat iron and steel products have final rolling speeds much larger than those of long products and they may attain 25 meters per second. Therefore a solution is therefore not in the integration time, because the intention today is to utilize automatic inspection devices operating on-line and at the production rate, this for minimizing costs.

In order to solve this problem of image formation in a different focal plane depending on the wavelength, certain camera manufacturers provide operation in the infrared by moving the focusing ring; often a red colour engraving is present on the focusing ring of the objectives. An empirical formula for calculating this displacement gives a shift of 0.0025 times the focal distance. But in fact this depends on the wavelength range used. The formula well-known to one skilled in the art, allows passing from visible light to a certain range of infrared light. But there exists a very extended range of this. Actually, the visible range is from 0.4 micrometer to 0.7 micrometer, there exists a near-infrared range between 0.7 and 3 micrometers, a medium infrared range between 3 and 25 micrometers and a far infrared range between 25 and 100 micrometers. All depends on the radiation from the body to be observed, therefore on its temperature. As regards the flat steel products at the exit of the hot-rolling mill, the temperature depends on the nature of the manufactured steel. The continual development of new touches of steel requires very accurate heat control during the hot-rolling and at the exit of the rolling mill up to the coiling of the strips, in particular for steels, the plasticity of which depends on their deformation, and which include phases in the metastable state. The outlet temperature may then currently vary today between 900° C. and 600° C. or less. It is therefore worthwhile to design a device which may also operate with far infrared light.

Furthermore, the methods proposed by camera manufacturers allow passing from visible light to a range of infrared light but the focusing for two images simultaneously derived from two lights cannot be obtained. Another solution would then be to use two cameras but the solution would be much more expensive, especially as colour cameras with three arrays for the three red, green and blue components of the usual cinema and television images are currently available, and as it is convenient to use an array in the infrared by simply setting up the adequate filter. Further, the method requires superposition of the images for processing contrasts by difference and this step of the method would be made much harder to achieve from images obtained from different cameras and objectives.

SUMMARY OF THE INVENTION

The present invention is directed to solving all these problems by a method which allows simultaneous observation of surface defects and defects present under the surface on hot products by allowing simultaneous focusing of the images acquired by means of infrared light emitted by the product and of visible light from additional illumination, reflected by the surface of the product.

According to the method of the invention, detection of the images of the hot product (S), formed for one part by light for which the wavelength is in the infrared region and for another part by light for which the wavelength is in the visible spectrum, is provided by several linear sensors (C1, C2, C3), each of them being associated with the detection of an image, set up in the same camera (4) and using the same objective (L), their axis being parallel to the line of sight (V', V), said sensors being each located in a different focal plane ($P_B$, $P_G$, $P_R$) associated with each wavelength range in order to obtain superposable images. Always according to the invention, the focal planes ($P_B$, $P_G$, $P_R$) of the different sensors (C1, C2, C3) are shifted relatively to the objective (L) by a distance corresponding to the correction of chromatic aberration of the objective for the various wavelengths used for forming and detecting each image.

Preferentially and according to the method of the invention, the light forming the part of the images for which the wavelength is in the infrared region is the light emitted by the hot product (S) itself during its travel.

According to the invention, the light forming the part of the images for which the wavelength is in the visible region is an additional illumination light of yellow, green or blue colour, sent onto the surface of the product during its travel. Advantageously, the colour of this additional illumination light is green.

According to the method of the invention, the images detected by the CCD sensors are analyzed in grey levels, acquisition of these images is synchronized among them and with the progress of the product (S) during its travel so as to be able to localize the detected defects relatively to the length of the product (S).

In the device of the invention, the sensors (C1, C2, C3) sensitive to each light spectrum are linear sensors, set up in a same camera (4), their axis being parallel to the line of sight (V', V), and in different focal planes ($P_B$, $P_G$, $P_R$), for this they are set up on a support (Q) tilted relatively to the optical axis (X', X) of the objective (L) of the camera (4).

According to another embodiment of the invention, the sensitive sensors (C1, C2, C3) are set up on a staged support (7), so as to be shifted along the direction of the optical axis (X', X) of the objective (L) of the camera (4) and found in different focal planes ($P_B$, $P_G$, $P_R$).

The device of the invention includes additional illumination means (2) with which light of yellow, green or blue colour may be projected onto the surface of the product (S).

In the device of the invention, the additional illumination means (2) of yellow, green or blue colour consist of light-emitting diodes.

According to a preferential embodiment of the invention, the device (1) for detecting defects includes protection means (3) and cooling means (6) of the image acquisition means.

According to a particularly advantageous embodiment of the invention, the additional illumination means (2) are integrated into the same protection means (3) as the means for acquiring images.

BRIEF DESCRIPTION OF THE DRAWINGS

But the invention will be better understood by the description of different embodiments.

DETAILED DESCRIPTION OF THE PREFERRED EMBODIMENT(S)

Figure 2:
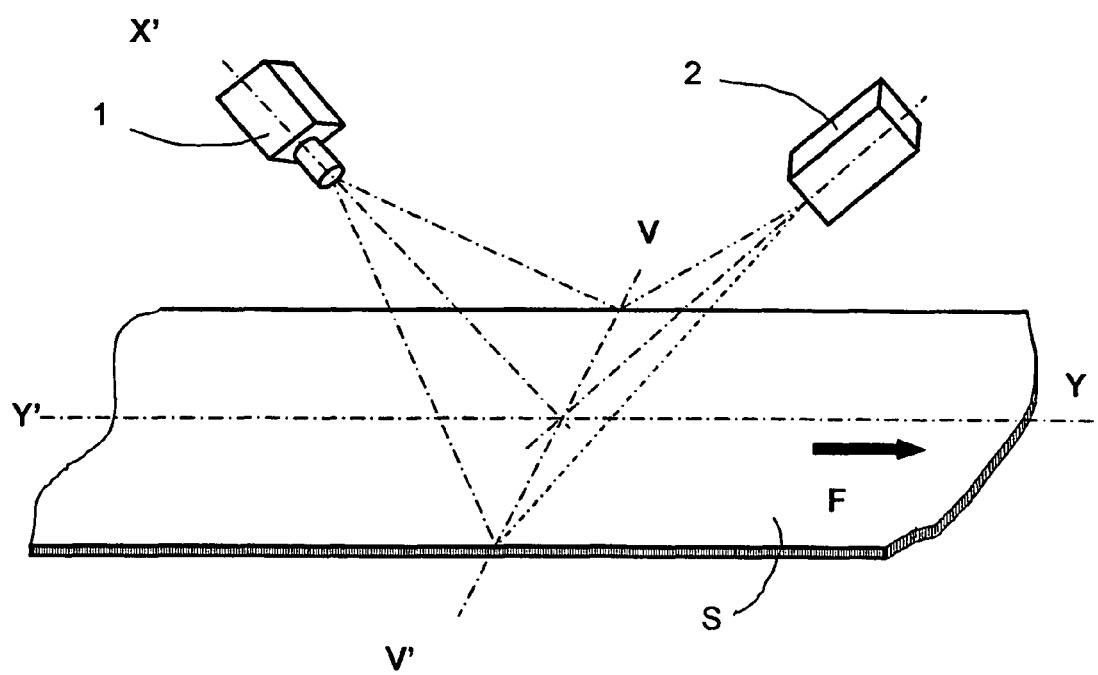
FIG. 2 is a general view of the device of the invention.

According to the invention shown in FIG. 2, the device 1 for detecting defects is oriented along its optical axis X'X towards the travelling product S.

A flat product was illustrated as this is the preferential case for applying the invention, but it may be applied to products for which the section has other shapes and other dimensions.

Many systems use the processing of images stemming from the product itself which radiates infrared light when it is hot. Other systems use auxiliary illumination devices 2 for illuminating the surface of the product to be observed and process the images derived from this illumination, generally located in the visible radiation range, and reflected by the surface of the product to be observed. In order to be able to detect the surface defects and also structural defects located under the surface, the inventive method processes images stemming from two kinds of light sources. Practically, the device 1 may be fitted with the illumination system 2 of the product S travelling in the F direction.

In the device of the invention, linear CCD sensors are used in the camera, the product may therefore be observed with the camera along a line of sight V'V which represents a strip illuminated by the illumination device 2 which may be separated from or integrated to the detection device 1. In the case of a flat product, the surface of the product is rather extended and the focusing method consisting of increasing the depth of field by closing the diaphragm cannot be used because the light has insufficient intensity, or else this would lead to more powerful and therefore more costly and more bulky illumination devices 2. Neither is it possible to use long exposure or integration times because the travelling speed of the product is high. Now, it is imperative to solve the problem of focusing in a different image focal plane for both kinds of light, because the processing of defects, according to the method of the invention, is performed in particular by superposition and comparison of the images.

Figure 1:
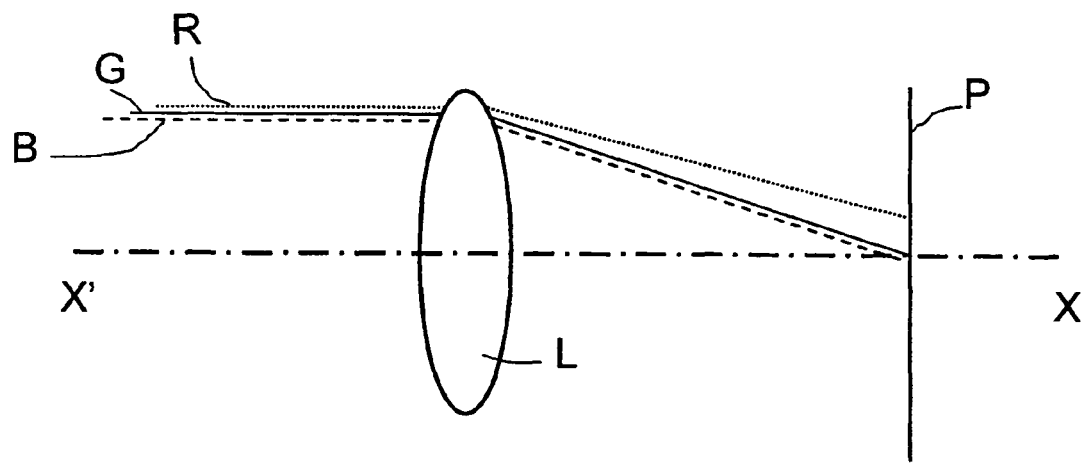
FIG. 1 illustrates the problem solved by the invention.

FIG. 1 illustrates the chromatic aberration phenomenon of the lenses. To simplify, a single convergent lens L is illustrated which gives a sharp image of an object located at infinity in an image focal plane P. The sensitive device, either a photographic plate or sensor, is set up in this focal plane and focusing is performed by moving the lens L. It is also possible to keep the lens fixed and to move the focal plane P. A lens produces refraction of the light rays at the boundary of the material in which it is made, with the ambient atmosphere. The particular geometrical shape which is given to this separation surface gives it special convergence, divergence properties or other properties.

A lens also behaves as a prism and has the property of breaking down the light. Its properties are different for the various wavelengths contained in the light which passes through it. According to this phenomenon, it is known that the shorter the wavelength of the light, the larger is the deviation. In FIG. 1, the path of a light ray corresponding to the green light G, was illustrated as a solid line, that of a ray corresponding to the blue light B, is illustrated as a dot and dash line, therefore more deviated by the lens L, and the path of a light ray located in the infrared R was illustrated as a dotted line. If the optical device is built and focusing is performed in the plane P for the range of visible wavelengths, the infrared image of the object which also radiates in this other range, will be formed at the rear of this focal plane P since the rays are less deviated, this second image will not be sharp and will not be superposable to the first.

In the general case, there is no solution to the focusing problem, except for those already mentioned, but the applicant company has observed that the object, the images of which are intended to be recorded, is a linear object. Indeed, detection of the defects is performed on a relatively narrow area of the travelling product S and oriented along the line of sight V'V. This area approximately corresponds to the illumination area made by means of the auxiliary illumination device 2. Therefore, the formed image is also linear and for this type of images, it is customary to use linear rather than matrix sensitive sensors since the images to be recorded are linear. Indeed, if linear images, the size of which is at least equal to the width of the product, are recorded at a sufficiently high frequency, sampling of said surface is achieved and it is possible to reconstruct images of it by means of digital processing by knowing the travelling speed. This is a well-known principle of scanners.

Now, the whole of the optical detection device 1 has a general cylindrical symmetry around the optical axis X'X. So that in fact, in the image focal plane P, a multiplicity of possible positions for the sensitive sensors are available, positions in which the image to be recorded is formed. The principle of the method of the invention is therefore to make use of this possibility by setting up several sensitive sensors, to associate each of them with the detection of an image formed by the light for which the wavelength is in a different range, and to shift the position of the sensitive sensor in the direction of the focal axis and depending on the wavelength of the light forming the image to be detected. With this, proper focusing in spite of the chromatic aberration phenomenon and images derived from different lights and nevertheless superposable may be achieved.

Figure 3:
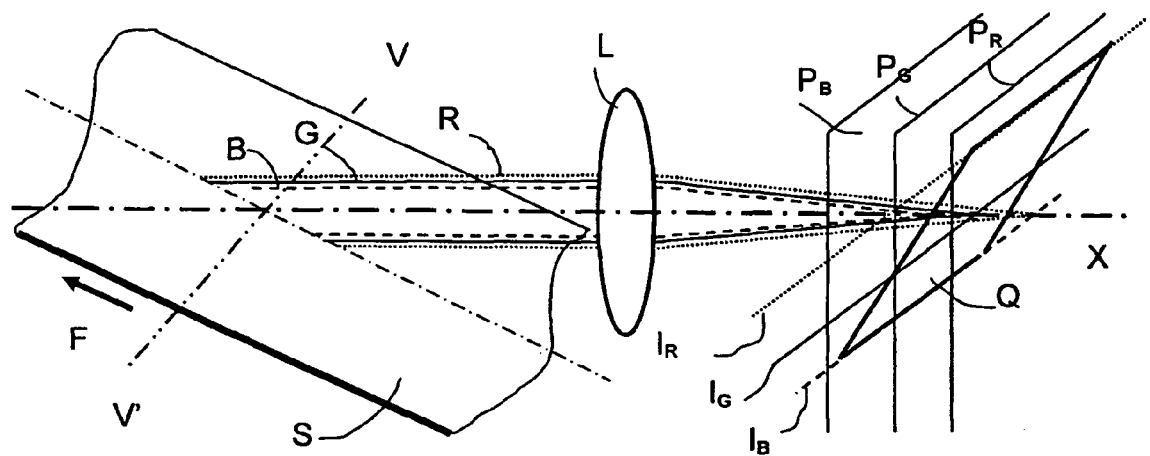
FIG. 3 illustrates the method of the invention.

FIG. 3 illustrates the inventive method. The travelling product S to be observed is illuminated along the line of sight V'V. This area is illuminated by the auxilia illumination device 2; moreover the product S is at a sufficient temperature for emitting infrared light, and this independently of the observed area.

The observation device 1 is oriented towards the middle line of the product S along its optical axis X'X, tilted relatively to the strip travel plane. The objective of the device 1 was symbolized by a convergent lens L with which images may be formed in the different image focal planes $P_B$, $P_G$ and $P_R$ depending on the wavelength range of the light which forms them. In industrial plants, the strip S is generally located so as to travel in a substantially horizontal plane. An image of the line of sight either horizontal or at least parallel to the object line of sight V'V is formed in each image focal plane. It is sufficient to set up a sensitive sensor in the $P_B$ plane, and in any position, but selected relatively to the distance from the optical axis in order to detect the whole image of the line of sight V'V. Indeed, the illuminated area is a strip, the image of which is also a strip in the focal planes. The linear sensors may be positioned at any location inside this image strip, and by recording successive images, a digital image of the surface of the product S may be reconstructed. If this sensor is equipped with a blue colour filter, an image $I_B$ of the line of sight for a wavelength corresponding to the blue colour will be obtained.

Also a sensitive sensor equipped with a green colour filter may be set up in the image focal plane $P_G$ in order to obtain a sharp image $I_G$ of the line of sight V'V for the wavelength corresponding to the green colour. This is the same for infrared light, with a sensitive sensor equipped with an infrared filter set up in the focal plane $P_R$, an image $I_R$ of the line of sight V'V may be obtained in the range of infrared wavelengths, i.e., within the scope of the invention, and formed by light stemming from the product S itself.

In a practical way, a position must be selected for each sensor at a certain distance from the optical axis in order to use the available space on either side of the optical axis X'X depending on the bulkiness of the selected sensors. It is convenient to define a plane Q containing the retained positions for the images $I_B$, $I_G$ and $I_R$ oriented along a direction orthogonal to the axis of the strip S and each contained in their respective focal plane $P_B$, $P_G$ and $P_R$. This plane Q is tilted relatively to the optical axis X'X and may be used as a support which will enable the positioning of sensitive sensors.

The empirical formula known to one skilled in the art gives a correction by a relative shift of the lens L with respect to the focal plane P, the value of which is equal to 0.0025 times the focal distance of the objective, and the applicant company was able to check during their experimentations that with this value, their devices for detecting defects were able to be focussed properly. With the optics currently used in the device of the invention with a focal distance of 50 millimeters, the correction to be made is of 0.0025×50=0.125 millimeters, i.e., 125 micrometers. Taking the sensor arrays used into account, it is possible to obtain the desired shift between the extreme wavelengths by installing a support inclined by 30° relatively to the optical axis. With these quite standard values in optical devices, the construction of the device 1 may perfectly be achieved industrially. Further, the luminosity loss caused by tilting the sensor is quite acceptable. Indeed, the light flux is attenuated by a value close to the value of the cosine of the tilt angle of the plane where the sensor lies, i.e., cos 30°=0.87 which corresponds to less than one diaphragm and which is a quite acceptable value as regards loss of luminosity.

Figure 4:
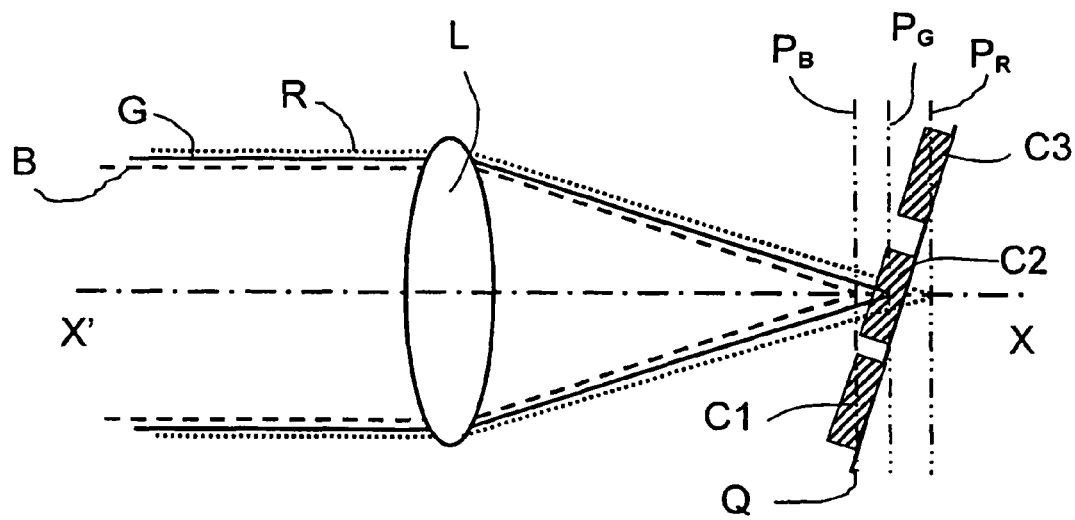
FIG. 4 is a diagram of an embodiment of the invention.

FIG. 4 very schematically illustrates an embodiment of the invention. In this illustration, the light beams emerging from the area of the line of sight have been magnified in order to facilitate the understanding of the principle of the invention. The sensors have also been enlarged for providing proper legibility to the drawing and are not illustrated to scale. The light beam emerging from the area of sight and containing the visible B, G and infrared R colours, enters into the optics of the device 1 illustrated by a convergent lens L. The images of the line of sight V'V are formed in planes $P_B$, $P_G$ and $P_R$ according to the colour of the light. A support for the sensors C1, C2 and C3 is positioned tilted on the optical axis along the plane Q. These sensors are located at a different distance from the optical axis, of course, they are all found in the area of the image of the illuminated strip surrounding the line of sight V'V. According to a preferential embodiment of the device of the invention, the sensors are linear CCD sensors, further designated as "charge transfer devices" and widely used today in digital imaging. Practically, a linear colour camera with CCD sensors is used, standardly equipped with three sensor arrays corresponding to the three fundamental colours of the usual colour images.

According to the invention, at least two of the arrays of a camera of this type are used and each is equipped with a particular filter. Thus, the arrays C1, C2 and C3 of sensitive CCD cells are preceded with colour filters F1, F2 and F3 respectively, one exclusively letting through the infrared wavelength, the others only letting through the wavelength of the additional light located in the visible region and of the selected colour. With this device of the invention, it is possible to differentiate between the acquisition of an image derived from infrared light and the acquisition of an image derived from the light emerging from the additional illumination device, and their separation, each on a different array, while allowing simultaneous acquisition of both images. These images are analyzed in grey tones and, as regards appearance and composition defects of the product, have localized areas which may be different because they may correspond to surface defects or defects under the surface.

With known algorithms for image processing installed in a computer, a mapping of the periphery of the product may be established by determinations and comparisons of the contours and contrasts. According to the method of the invention, at least two arrays of sensitive sensors will be used, one operating in the infrared region and the other in the visible region, in order to record the images obtained with the additional illumination device 2. But, if need be, the third array available in a determined wavelength range may be used for increasing the detection capabilities of the system and without departing from the field of the invention.

Figure 5:
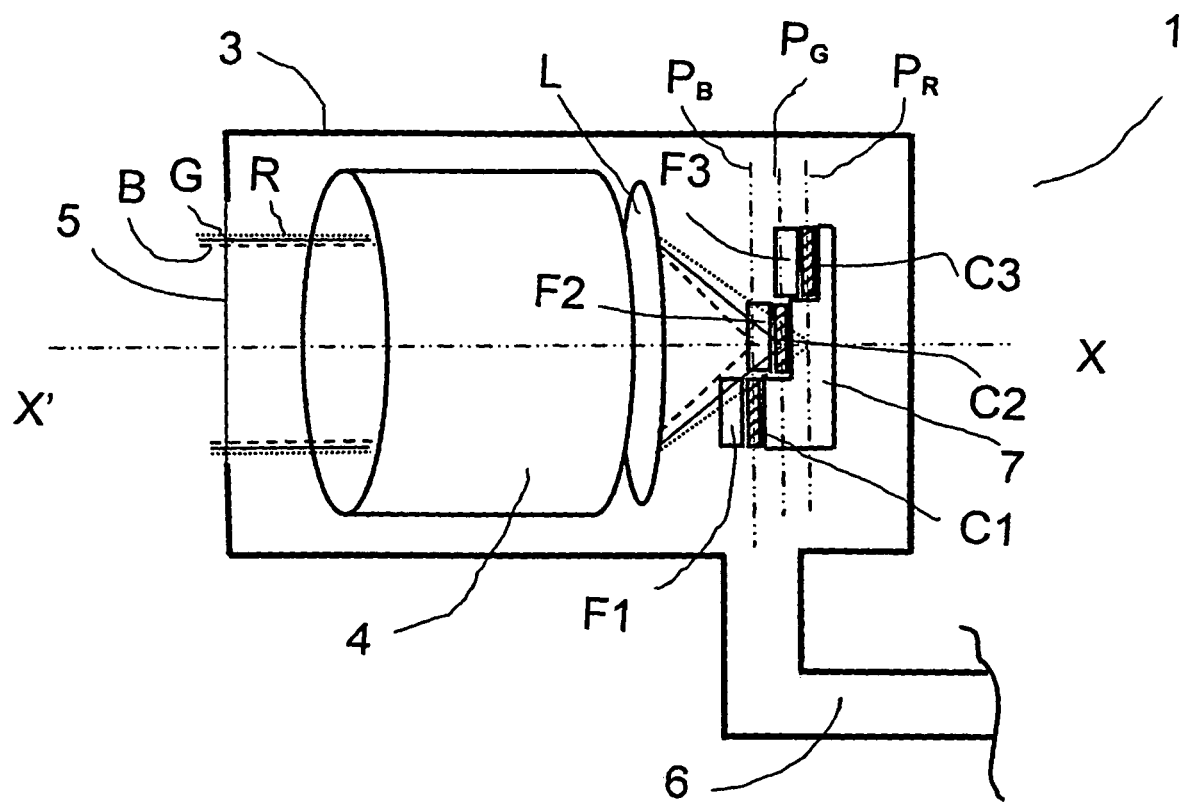
FIG. 5 is a diagram of another embodiment of the device of the invention.

According to an enhanced embodiment of the invention, a shift of the focal planes may also be obtained without causing any attenuation, even minimal of the light flux. This embodiment is illustrated in FIG. 5 which also shows more completely the whole of the embodiment of the device according to the invention.

The device 1 for detecting defects is oriented along the optical axis X'X towards the middle portion of the strip to be observed. The whole 1 is protected by a rigid box 3 preferably in metal, so that it may be set up in a severe environment of a hot production line such as a hot-rolling line and in immediate proximity to the product. The box 3 is leakproof and completely sealed; it is cooled and ventilated by air blowing by means of the conduit 6. With a fine transparent area 5 located on the front face of the box 3, it is possible to receive the lights emitted by reflection and natural diffusion from the product to be observed S. The whole of the camera 4 includes an objective schematized in FIG. 5 by the convergent lens L and sensitive sensors C1, C2 and C3 mounted as arrays. An embodiment of the invention using three arrays of a standard colour camera is illustrated, but as already stated, the method of the invention may be applied by using a minimum of two arrays.

The light schematized by the rays of blue B, green G and infrared R colours penetrates into the camera 4. Image planes $P_B$, $P_G$ and $P_R$ are formed at the focal distance of the lens L, shifted according to the wavelength used. A support 7 for the arrays is provided with spaces in the form of stairs, shifted by the distance required for the different focalizations, in order to receive the sensors C1, C2 and C3. The sensors are each equipped with a filter F1, F2 and F3 of the colour which is intended to be used to form an image.

As a non-limiting example, if the intention is to design a device for detecting defects operating in the infrared light emitted by the product and in the light of an auxiliary illumination, for example a green light, the camera 4 will be equipped with two arrays of sensors C1 and C2 fitted with a green filter F1 for the sensor C1 and an infrared filter F2 for the sensor C2. The support 7 will include two machined levels with a shift given by the Kodak formula, i.e., 125 micrometers for an objective, the focal distance of which would be 50 millimeters.

In all these devices, the cameras are connected to image acquisition, synchronization, interface devices and to image processing computers including pattern and contrast recognition software packages, as well as storage units, not shown in the figures. All these devices have been the subject of descriptions in other patent applications and it is unnecessary to repeat them here.

According to the method of the invention, the camera 4 by correcting the chromatic aberration of the objective, may detect sharp and superposable images of the area of the product to be observed located along the line of sight V'V. The signals of the photo-electric cells forming the CCD sensors are then analyzed in grey levels and the images from the emission produced by the product and from the reflection produced by its surface are compared. The results are stored and compared with reference images located in a library memory of defects so as to be able to explicitly report a certain number of types of defects. Of course, the invention is not limited to the embodiment which has just been described as an example, and may be applied to detecting defects of steel products or consisting of another metal and of different forms without departing from the scope of the invention.

The invention may also be applied to any product of another material or elaborated by a method other than rolling, such as for example hot extrusion of plastics.

It is also possible to use other arrangements of CCD cells, of optics and filters, in order to correct the chromatic aberration of the lenses for achieving acquisition of sharp and superposable images derived from the lights located in at least two different wavelength bands without departing from the scope of the invention.

Different types of photosensitive sensors may also be used without departing from the scope of the invention.

Finally the idea of using recognition, processing and image comparison algorithms other than those mentioned earlier, may be devised, such as for example those used in processing cinema and television images for special effects or colorization of black and white images without departing from the field of protection given by the claims.

The reference signs inserted after the technical features mentioned in the claims, have the sole purpose of facilitating the understanding of the latter and by no means limit their scope.

The invention claimed is:

1. An optical method which detects defects of a hot traveling product having a temperature typically within the range of 600-1000° C. during hot-rolling, the method simultaneously detecting defects located on a surface and under the surface of the hot traveling product by the formation and processing of images of the hot traveling product, the images formed by a first portion from light emitted by the hot traveling product itself and for which the wavelength is in the infrared region and by a second portion from light reflected by the product and for which the wavelength is in the visible spectrum, the detection of the lights being provided by a plurality of linear sensors, each of the linear sensors being associated with the detection of an image, the method comprising:

provide linear sensors collectively arranged relative to an objective of a camera, with each of the linear sensors being located in a different focal plane associated with a wavelength range in order to obtain superposable images;

moving the linear sensors relative to the objective depending upon the wavelength of light forming an image to be recorded, each of the linear sensors being movable to a multiplicity of positions relative to the objective; and providing a defect detection signal obtained from the linear sensors.

2. The optical method of claim 1, wherein the focal planes of the linear sensors are shifted relative to the objective by a distance corresponding to a correction of the chromatic aberration of the objective for the different wavelengths.

3. The optical method of claim 1, wherein the light forming the second portion of the image for which the wavelength is in the visible region is an additional illumination light of yellow, green, or blue color, and is sent onto the surface of the hot traveling product.

4. The optical method of claim 3, wherein the additional illumination light is of green color.

5. The optical method of claim 1, wherein the light received by the linear sensors is analyzed in grey levels.

6. The optical method of claim 5, wherein the forming and processing of the images is synchronized among the images and with the progress of the hot traveling product during its travel, so as to be able to localize the detected defects relative to the length of the hot traveling product.

7. An optical device which detects the defects of a hot traveling product having a temperature typically within the range of 600-1000° C., the optical device including:

a forming unit which forms images of the hot traveling product, the forming unit comprising a camera and an objective;

a plurality of linear sensors arranged relative to the objective and which detect the formed images, each of the linear sensors being sensitive to respective different spectrums of light sent by the camera using the objective;

each of the linear sensors being located in a different focal plane and being moveable relative to the objective to a multiplicity of positions within that plane depending upon a wavelength of light forming the image; and an image processor which processes the detected images of the hot traveling product, the processing comprising analyzing images formed by a first portion from light for which the wavelength spectrum is located in the infrared region, and by a second portion from light for which the wavelength spectrum is located in the visible region.

8. The optical device of claim 7, wherein the plurality of sensors are set up on a support tilted relative to an optical axis of the objective.

9. The optical device of claim 7, wherein the plurality of sensors are set up on a staged support so as to be shifted along a direction of an optical axis of the objective.

10. The optical device of claim 7, wherein the forming unit, the plurality of sensors, and the image processor associate infrared light emitted by the hot traveling product itself and visible light emitted by an additional illumination apparatus, the visible light being of yellow, green, or blue color, and being projected onto the surface of the hot traveling product.

11. The optical device of claim 10, wherein the visible light emitted by the additional illumination apparatus is of green color.

12. The optical device of claim 10, wherein the additional illumination apparatus includes light emitting diodes.

13. The optical device of claim 7, further including: a protection apparatus; and a cooling apparatus.

14. The optical device of claim 13, wherein an illumination apparatus is integrated into the protection apparatus.

15. The optical method of claim 1, wherein each of the linear sensors has respective axes parallel to a line of sight substantially perpendicular to a direction of travel of the hot traveling product.

16. The optical method of claim 1, wherein the second providing step is followed by a transmission of the defect detection signal to an image processing means for processing images and an analysis of the light received by the linear sensors.

17. The optical device of claim 7, wherein the plurality of sensors have axes parallel to a line of sight substantially perpendicular to a direction of travel of the hot traveling product.

* * * * *